United States Patent [19]

Borrelly

[11] Patent Number: 4,790,313
[45] Date of Patent: Dec. 13, 1988

[54] SEALING DEVICE FOR TUBING

[76] Inventor: Jacques Borrelly, 1 rue de la Vigne des Sables, 54180 Heillecourt, France

[21] Appl. No.: 906,062

[22] Filed: Sep. 11, 1986

[30] Foreign Application Priority Data

Sep. 13, 1985 [FR] France ................. 85 13580

[51] Int. Cl.$^4$ .............. A61B 17/04; A61M 29/00; F16L 55/12
[52] U.S. Cl. ................ 128/334 R; 604/96; 138/93; 623/12
[58] Field of Search ............ 285/97, 382.4; 604/96, 604/280, 282, 43; 623/1, 12, 9; 138/93; 128/344, 334 R

[56] References Cited

U.S. PATENT DOCUMENTS

| | | | |
|---|---|---|---|
| 2,883,986 | 4/1959 | Luca et al. | 604/96 |
| 3,154,077 | 10/1964 | Cannon | 128/344 |
| 3,190,679 | 6/1965 | Lester | 138/93 |
| 3,890,976 | 6/1975 | Bazell et al. | 604/96 |
| 4,406,656 | 9/1983 | Hattler et al. | 604/96 |
| 4,550,751 | 11/1985 | Shimamura et al. | 138/93 |
| 4,609,042 | 9/1986 | Broadus | 138/93 |

Primary Examiner—Richard C. Pinkham
Assistant Examiner—Gary Jackson
Attorney, Agent, or Firm—Sughrue, Mion, Zinn, Macpeak, and Seas

[57] ABSTRACT

A sealing device includes a tubular central core (1, 40, 61) of generally U-shaped cross section. The central core has a degree of elasticity to deformation of its shape in a plane perpendicular to its longitudinal direction (2). A membrane (5, 41, 65) is disposed around said central core. The membrane is made of a flexible and elastic material having a much higher coefficient of elasticity than the central core. The membrane is sealed with edges of side walls (15) of the central core and at the longitudinal end of the membrane to the core to form a closed deformable chamber (8, 42, 68) of substantially crescent-shaped cross section. A fluid under pressure is admitted to the inside of the chamber (8, 42, 68).

11 Claims, 3 Drawing Sheets

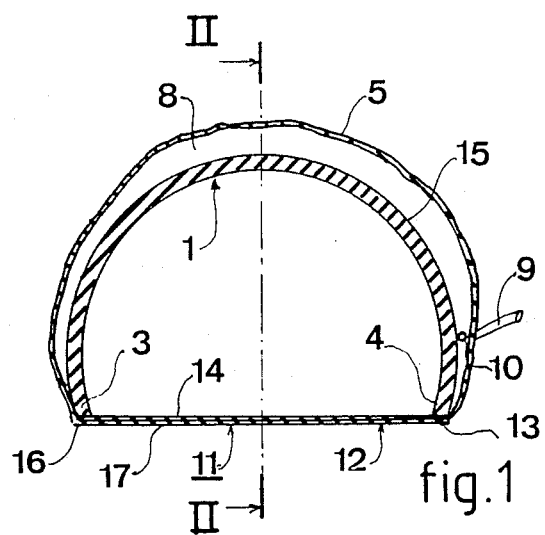
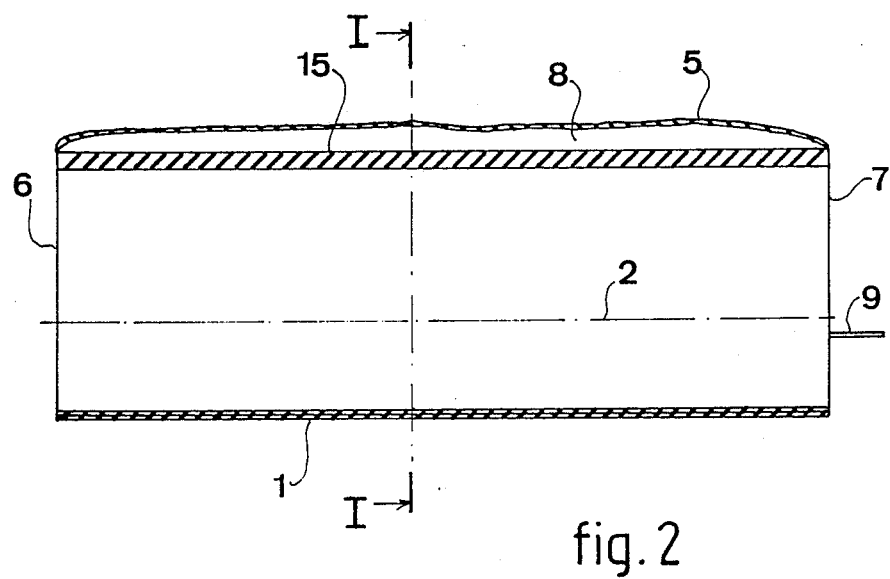

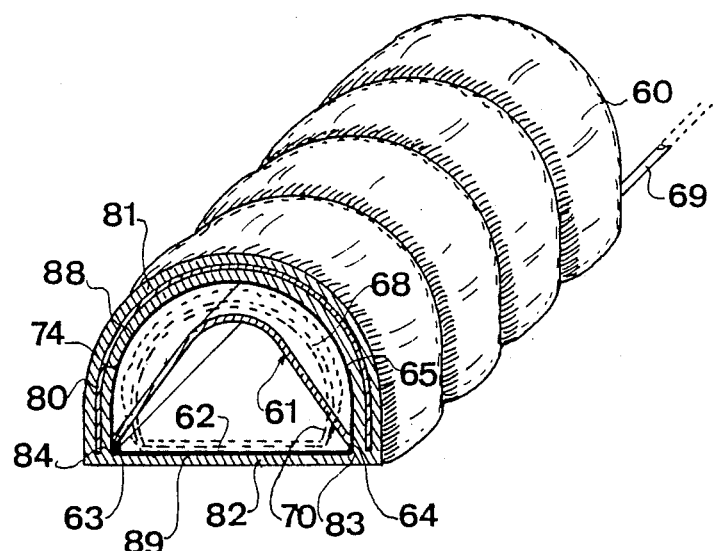
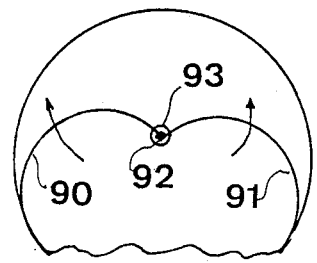
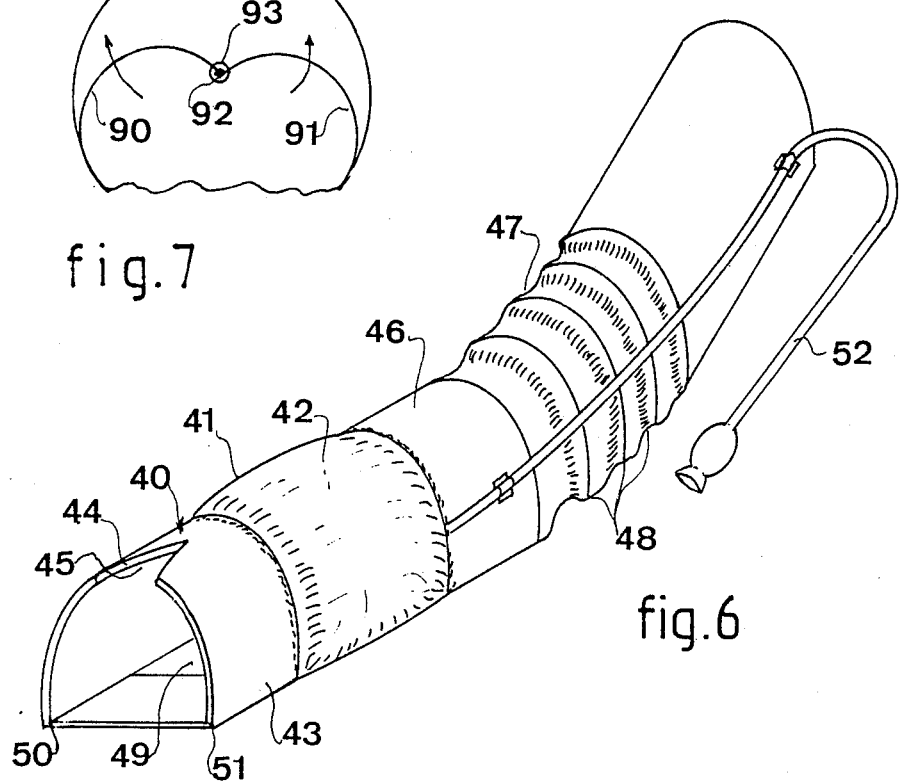

SEALING DEVICE FOR TUBING

The preset invention relates to sealing devices for use inside tubing, for example devices which seal or close off a leak from tubing by pressing a pad against the inside surface of the tubing.

BACKGROUND OF THE INVENTION

In many fields and for various reasons, there is often a need to provide sealing, e.g. by closing off an opening in tubing, and this applies regardless of whether the opening is provided deliberately or by accident. However, in some cases it is not always easy to gain access to the outside of the opening through the tubing in order to press any kind of closure pad thereover.

Techniques have therefore been developed to provide sealing or closure from the inside of the tubing. A pad is inserted into the tubing having an opening and is then pressed against the opening from the inside. In order to obtain good sealing when pressing a pad over an opening, various factors need to be taken into consideration, for example the nature of the materials used, i.e. the tubing material and the pad material. An important one of such factors is the force or pressure applied to the pad, and in particular the effective force or pressure around the edges or margin of the opening.

When a pad is applied to the outside of tubing, it is generally fairly easy to ensure that a desired amount of force is used and in particular to find an easily accessible bearing point or surface from which to apply the force. In contrast, when closing an opening from inside the tubing, finding a suitable bearing point is more difficult, particularly when the tubing is to continue to convey a flow of fluid (gas or liquid).

Special closure structures have already been made to solve this problem. These structures comprise a central core constituted by a rigid cylindrical sleeve forming a portion of continuous ducting, with the outside diameter of said portion of ducting being less than the inside diameter of the tubing to be sealed. A flexible resilient membrane is placed around the sleeve and is fixed in sealed manner at each of its ends to the ends of the sleeve so as to form an deformable sealed annular chamber around the sleeve. A small pipe is provided for admitting a fluid, e.g. a gas, under pressure into said annular chamber, thereby allowing it to be inflated at will.

In order to seal an opening in tubing, this structure is inserted inside the tubing and the free end of the small pipe is kept accessible from the outside. When the membrane is properly located facing the opening, fluid is injected at a predetermined pressure via the small pipe. The annular chamber is thus inflated, and as it inflates a portion of its outside surface is pressed closely against the entire inside surface of the tubing, including the opening and the wall around the opening.

The opening is closed by pressing a pad constituted by the portion of the membrane which presses against the rim of the opening, with the force applied being determined by the pressure inside the annular chamber and with the bearing surface providing a reaction to said force being constituted by the surface of the tubing which comes into contact with the membrane forming the outside wall of the annular chamber. The rigid cylindrical sleeve is thus located substantially in the middle of the tubing, thereby ensuring continuity for fluid flow.

This technique gives very good results in any tubing having a wall which is capable of withstanding pressure over its entire surface area.

However, there exist various kinds of tubing whose walls cannot withstand pressure over their entire surface area. This applies, for example, in medical applications concerning the trachea (i.e. the windpipe).

The trachea is generally tubular, but is definitely not a circular cylinder, and it is made up of two portions. The first portion is gutter-shaped, having a generally U-shaped cross section, and it is relatively rigid by virtue of reinforcing cartilage. The second portion interconnects the two longitudinally-extending edges of the gutter. This second portion is fibrous, and very flexible to the point of being fragile.

Thus, when applying forced ventilation to a patient via the trachea, it is highly dangerous to provide peripheral sealing by means of a structure of the type described above because of the fragile second portion of the trachea.

Preferred implementations of the present invention provide a device for sealing tubing while avoiding the above drawback, said device being particularly applicable to closing an opening through the wall of tubing and to providing peripheral sealing around the opening when the tubing in question is a trachea.

SUMMARY OF THE INVENTION

The present invention provides a sealing device for tubing, said device comprising:

a tubular central core of generally U-shaped cross section, said central core having a degree of elasticity to deformation of its shape in a plane perpendicular to its longitudinal direction;

a membrane disposed around said central core said membrane being made of a flexible and elastic material having a much higher coefficient of elasticity than said central core, said membrane being associated in sealed manner with the side wall of said central core to form a closed deformable chamber of substantially crescent-shaped cross section; and means for admitting a fluid under pressure to the inside of said chamber.

BRIEF DESCRIPTION OF THE DRAWINGS

Embodiments of the invention are described by way of example with reference to the accompanying drawings, in which:

FIGS. 1 and 2 are two perpendicular sections through a device embodying the invention;

FIG. 5 shows a device in accordance with the invention being applied to providing peripheral sealing in a trachea:

FIG. 6 shows another embodiment of a device in accordance with the invention suitable for providing, in addition, the function of a cannula for tracheotomy; and FIG. 7 is a diagrammatic cross section through one embodiment of an essential component of a device in accordance with the invention.

MORE DETAILED DESCRIPTION

Figure 3:
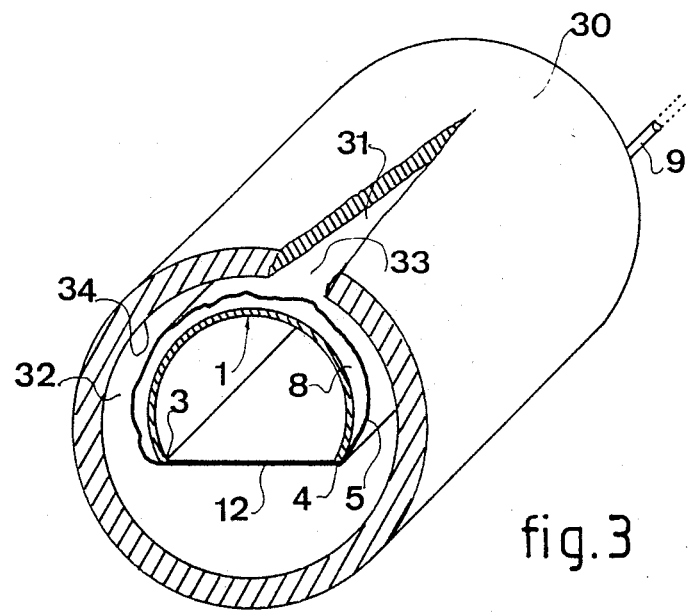
FIGS. 3 and 4 show a device in accordance with the invention being applied to closing an opening through the wall of cylindrical tubing.

FIGS. 1 and 2 are two perpendicular sections through a first embodiment of a sealing device in accordance with the invention. FIG. 1 is a cross section on a line referenced I—I in FIG. 2, and FIG. 2 is a longitudinal section on a line referenced II—II in FIG. 1.

The device in accordance with the invention comprises a central core 1 which is advantageously in the form of an incomplete cylinder having a cross section in the form of an arc of a circle. The central core 1 is made of material having a degree of elasticity for deformation in a plane perpendicular to its longitudinal axis 2 (see FIG. 2), i.e. in planes parallel to the section I—I shown in FIG. 1. This material may be a semi-rigid material pre-formed to the shape of an incomplete cylinder. Thus, when a force is applied to move its longitudinal edges 3 and 4 apart, the core deforms by opening somewhat, and when the force is released it returns to its initial shape as shown in FIG. 1.

A flexible elastic membrane 5 is fixed to the central core 1. The membrane 5 is fixed to the edges of the central core 1, i.e. both to its rectilinear longitudinal edges 3 and 4 and also to its arcuate end edges 6 and 7, thereby constituting a closed deformable chamber 8 with a generally crescent shaped cross section. In order to ensure that the chamber is properly sealed, the edges of the membrane are either glued or welded to the edges of the central core.

In an embodiment which is advantageous in some applications, the longitudinal edges 3 and 4 of the central core 1 are interconnected by resilient means 11 which act as a tensioner.

The resilient means may be constituted by a traction spring connected at its ends to the edges 3 and 4 and tending to oppose any tendency of the edges to move apart.

Alternatively, the resilient means 11 may be constituted by an interconnecting membrane 12 which may form a part of the chamber-forming membrane 5. In this case, the membrane 5 is constituted by a tubular sleeve which completely surrounds the central core 1. However, the sleeve is still sealed to the longitudinal edges 3 and 4 of the central core, thereby forming both the sealed chamber 8 and the resilient means 11.

In another advantageous embodiment, the interconnecting membrane 12 may be constituted by two superposed portions of membrane, and in practice this is achieved by overlapping opposite marginal strips of the same membrane.

This is done by taking a membrane which is longer than the peripheral distance round the central core 1. One end 13 of the membrane is fixed to the longitudinal edge 4, the membrane is then stretched linearly over to the opposite edge 3 and is fixed thereto, leaving a generally planar membrane portion 14 under tension between the edges 3 and 4. The membrane is then wrapped round the curved outer surface 15 of the central core 1 and returns to the first edge 4, where it begins to overlap the portion 14 under tension. The second end 16 of the membrane is then fixed to the membrane portion 14 where it is itself fixed to the other edge 3.

Thus, the interconnecting membrane 12 extending between the longitudinal edges 3 and 4 provides resilient means that are stiffer than would be provided by a single sheet of membrane, and are also stronger, which may be advantageous in some applications.

A small pipe 9 has one end 10 in sealed communication with the inside of the chamber 8 so as to enable the chamber 8 to be inflated by means of fluid at a determined pressure, as described below.

The above-described sealing device is intended for sealing tubing from the inside, said tubing having an opening such as a slot, tear or gash, for example.

Figure 4:
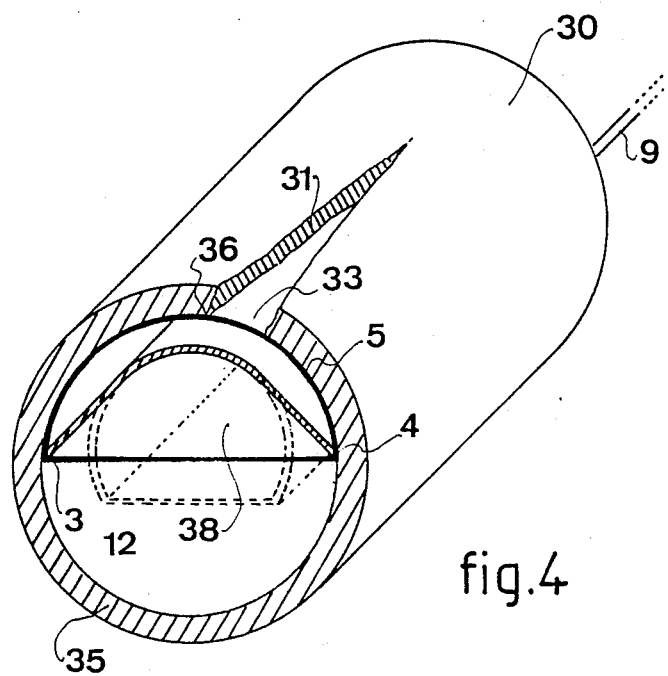

FIGS. 3 and 4 show the device being used to seal a tube 30 having a slot 31 said tube 30 including a wall portion 35 which should not be used to provide a bearing surface.

FIGS. 3 and 4 show the sealing device in cross section and in two different positions: the first position shown in FIG. 3 being its position for insertion into the tube; and the second position shown in FIG. 2 being its position for closing the slot 31.

FIGS. 3 and 4 thus show two stages in the process of closing the slot 31 in the wall of the tube 30. The sealing device is large enough to ensure that the circumferential extent of the membrane 5 is considerably greater than the width of the slot 31. The device is inserted into the tube and held in such a position as to bring the membrane 5 into the proximity of the slot 31, or at least into the proximity of the opening 33 of the slot 31 through the inside surface 34 of the wall of the tube 30. The plane portion 12 extending between the longitudinal edges 3 and 4 of the device faces the portion 35 of the tube wall which includes weak points making it unsuitable for use as a bearing surface.

The far end of the small pipe 9 extends freely to the outside of the tube. Other means are used for holding the membrane 5 and the central core 1 in the proximity of the slot 31. When the device is positioned as shown in FIG. 3, gas is injected under pressure into the small pipe 9 thereby inflating the deformable chamber 8. Initially the membrane 5 stretches on its own, then with increasing pressure inside the chamber 8, the central core 1 deforms so that its longitudinal edges 3 and 4 tend to move apart and apply tension to the resilient membrane 12 which holds them together. With progressively increasing pressure, the edges 3 and 4 come into contact with the inside surface 34 of the tube 30, and the membrane 12 stretches without coming near to the relatively fragile portion 35 of the tube wall. Once the edges 3 and 4 have come into contact with the inside surface 34 of the tube 30, the membrane 5 is again subjected to deformation by increasing gas pressure and spreads itself evenly over the entire facing area of the inside surface 34 of the tube 30, thereby pressing itself against the perimeter 36 of the opening 33 of the slot 31 in the inside surface 34.

The pressure is adjusted so that the device remains firmly pressed against the inside surface 34 by virtue, in particular, of reaction and friction forces, but avoiding any possibility of it deforming so much that it presses against the fragile portion 35 of the tube wall. The deformation of the central core 1 so that it tends to open when the chamber 8 is inflated is a known physical phenomenon, and the membrane presses evenly against the inside surface 34 of the tube wall as the chamber is inflated, thereby coming into close contact with the edges of the slot and thus completely closing it off.

It can thus be seen that under these conditions the membrane 5 constitutes a pad which completely closes the slot 31, while the membrane 12 has no tendency to press against the portion 35 of the tube 30. The portion 35 may be a fragile portion which is not stiff enough to act as a bearing surface, i.e. which cannot provide the reaction force necessary for keeping the pad pressed over the slot 31. The required reaction force is provided solely by that portion of the inside surface 34 of the tube against which the device comes into contact. The device is thus effective from inside the tube 30 to hold the membrane 5 against the slot 31, thereby completely closing the slot.

The above-described mode of using a device in accordance with the invention in an application to sealing a tube having a slot through its wall is given, by way of example, to show the invention being used in a general context. However, the invention is particularly advantageous for use in the context of providing peripheral sealing in the trachea (i.e. the windpipe) of a patient who is being ventilated artificially.

FIG. 5 shows an embodiment of the sealing device for use in providing peripheral sealing in a trachea. In this case, dashed lines 70 show the shape of the device as it is being inserted into the trachea 60. Once the sealing device is in place, fluid is inserted at controlled pressure via the free end of the inflation pipe 69 so as to inflate the crescent-shaped chamber 68 and press the membrane 65 against the inside surface 74 of the trachea and to deform the central core 61 in the manner explained above. The central core 61 deforms so that its longitudinal edges 63 and 64 come as close as possible to the inside corners 83 and 84 in the trachea where the semicircular cartilage-reinforced wall 81 including its semicircular ring 80 comes into contact with the substantially plane fibrous wall 82. Thus, the membrane 62 interconnecting the longitudinal edges 63 and 64 in a substantially rectilinear manner, lies parallel to the fibrous wall 82 and comes lightly into contact therewith, thus providing lateral sealing by friction in order to avoid deforming the fibrous wall which is very fragile.

A patient's breathing may thus be assisted mechanically by blowing air between the membrane 62 and the central core 61 without leaks occuring between the inside surface of the trachea and the longitudinal side wall surrounding the device, either at the contact surface 88 where the inside surface 74 of the semicircular wall 81 comes into contact with the outside surface of the crescent-shaped membrane 65, or at the contact surface 89 where the inside surface of the fibrous wall 82 comes into contact with the outside surface of the membrane 62 which interconnects the longitudinal edges 63 and 64 in a substantially rectilinear manner.

The advantage of such a sealing device can thus be seen in the specific application of assisting respiration via the trachea, with the device enabling air to be blown between its central core 61 and its membrane 62 without leakage and without deforming the fragile fibrous wall 82.

FIG. 6 shows another embodiment of a sealing device of the kind shown in FIGS. 1 to 4. However, in this case the central core 40 is much longer than the membrane 41. In particular, the core 40 extends beyond each of the ends of the deformable chamber 42.

The portion 43 of the core which projects beyond the leading end of the chamber 42 extends only a short distance and serves to provide an abutment 44 for engaging an element located inside the tubing to be sealed. If the tubing is a trachea, the leading end may include a notch 45 for fitting more easily against the fork between the left and right bronchi. In this case the abutment is advantageously made of flexible material in order to avoid damage, and it may also include sealing means.

In contrast, the other end portion 46 of the core extending beyond the other end of the chamber is long and may include articulations 47 providing some degree of rotation if required. The articulations 47 may be constituted by a series of corrugations 48 in the wall of the central core to constitute a bellows-portion. This configuration makes it possible to insert the sealing device into the tubing to be sealed, even if the tubing includes portions which are slightly curved. This configuration is advantageously applicable to artifically ventilating a patient by tracheotomy, in which case the bellows portion is advantageously situated at the junction between the portion of the device which is inserted into the trachea and the outside portion of the device.

As mentioned above, the sealing device advantageously includes a tension membrane 49 extending between the edges 50 and 51 of the gutter-shaped central core 40 in order to compensate for the force due to deformation when the deformable chamber 42 is put under pressure. Under certain conditions the membrane 49 may be extended to completely close the gutter and to turn it into a tubular duct over its entire length. This duct can then be used, still within the context of the present invention, to constitute means for injecting some other fluid into the tubing for any reason, for example to constitute a tracheotomy cannula for ventilating a patient. An inflation pipe 52 is associated with the deformable chamber as explained above with reference to FIGS. 1 and 2 for inflating the U-shaped chamber 42 and it runs along the portion 46 of the core.

In a particular embodiment, when the inside dimensions of the tubing to be sealed are known relatively accurately in advance, the membrane 49 may be constituted by non-resilient link means of fixed maximum length, but capable of folding, for example, in order to avoid deforming the tube between the edges 3 and 4 of the central core 1. The maximum length of the membrane is then equal to the chord interconnecting the inside 5 of the tube 30 between points 3 and 4 (FIG. 4) or 83 and 84 (FIG. 5).

Finally, in another embodiment, the central core may advantageously be constituted, as shown diagrammatically in FIG. 7, by two right circular cylinder portions 90 and 91 coupled together in sealed manner about a hinge 93 running along a generator line 92 common to both cylinder portions. Such a hinge allows the central core to deform in a manner analogous to elastic deformation as described above.

I claim:

1. A medical sealing device for sealing tracheal tubing, said device comprising:

a tubular central core of generally U-shaped cross section having opposed ends and sidewalls defining laterally spaced longitudinal edges, said central core having a degree of elasticity to deformation of its shape in a plane perpendicular to its longitudinal direction;

a membrane disposed around said central core having opposed ends, said membrane being made of a flexible and elastic material having a much higher coefficient of elasticity than said central core, the opposed ends of said membrane being sealed to the outer periphery of the U-shaped cross section central core and said membrane further being sealed at the side wall edges of said central core to form an external, closed deformable chamber of substantially crescent-shaped cross section;

resilient traction means interconnecting the longitudinal edges of said central core of U-shaped section; and means for admitting a fluid under pressure to the inside of said chamber, whereby when said device is inserted within a tracheal tube of a diameter in excess of the diameter of the U-shaped cross section central core, pressurization of the chamber causes the membrane to stretch and the central core to deform so that its longitudinal edges tend to move apart and apply tension to the resilient membrane tending to cause the edge of the central core to contact with the inside surface of the tube and under further increased pressurization, the membrane is subjected to further deformation and spreads itself evenly over the entire facing area of the inside surface of the tube for closing off any leaks within the tube by surface contact therewith.

2. A device according to claim 1, wherein said resilient traction means are constituted by an elastic wall.

3. A device according to claim 2, wherein said elastic wall is constituted by a portion of said membrane disposed around said central core.

4. A device according to claim 2, wherein said elastic wall is constituted by two overlapping end portions of said membrane.

5. A device according to claim 1, wherein said central core is longer than said chamber.

6. A device according to claim 5, wherein a portion of said central core situated to one end of said chamber includes abutment means.

7. A device according to claim 5, wherein a portion of said central core situated to one end of said chamber includes articulation means.

8. A device according to claim 7, wherein said articulation means is constituted by a portion of said central core having corrugations constituting a bellows.

9. A device according to claim 1, wherein the two longitudinal edges of the central core are connected to a sealing membrane over their entire length.

10. A device according to claim 1, including link means interconnecting the longitudinal edges of said central core of U-shaped cross section, said link means determining a maximum length.

11. A device according to claim 1, wherein said central core is built up from at least two portions of substantially circular cylinders together with sealed hinge means between said two portions of cylinders.

* * * * *